(12) United States Patent
Atwood (10) Patent No.: US 7,014,868 B2
(45) Date of Patent: Mar. 21, 2006

(54) HEXAMERIC COMPLEXES AND THEIR PREPARATION

(75) Inventor: Jerry L. Atwood, Columbia, MO (US)

(73) Assignee: Curators of the University of Missouri, Columbia, MO (US)

( * ) Notice: Subject to any disclaimer, the term of this patent is extended or adjusted under 35 U.S.C. 154(b) by 205 days.

(21) Appl. No.: 09/978,925

(22) Filed: Oct. 16, 2001

(65) Prior Publication Data

US 2003/0073872 A1    Apr. 17, 2003

(51) Int. Cl.
*A61K 9/14* (2006.01)
*A61K 39/12* (2006.01)

(52) U.S. Cl. .................. 424/489; 568/719; 977/DIG. 1
(58) Field of Classification Search ................ 424/451, 424/486; 568/719, 722; 977/DIG. 1
See application file for complete search history.

(56) References Cited

FOREIGN PATENT DOCUMENTS

JP            10245353 A   *   9/1998

OTHER PUBLICATIONS

Gerkensmeier, et al., "Self-Assembly of 2,8,14,20-Tetraisobutyl-5,11,17,23-tetrahydroxyresore[4]arene," Eur. J. Org. Chem., pp. 2257-2262, (Jan. 11, 1999).

MacGillivray, Leonard R. et al, "" A chiral spherical molecular assembly held together by 60 hydrogen bonds", " Nature, p. 469-472, (Oct. 2, 1997).

* cited by examiner

*Primary Examiner*—Michael Hartley
(74) *Attorney, Agent, or Firm*—William D. Jackson (57) ABSTRACT

A composition comprising a guest/host assembly having a spheroidal host assembly comprised of a hexamer of a methylene-bridged trihydroxybenzene tetramer and a guest component encapsulated within the spheroidal host assembly to provide a highly stable guest/host assembly. A guest component, specifically a pharmaceutically active agent, is encapsulated within the spheroidal host assembly to provide a guest/host assembly exhibiting a high stability, being stable upon a solubilization in a mixture of acetone and water in a one-to-one ratio for a period of one day at a temperature of 37° C. The pharmaceutically active agent encapsulated within the spheroidal hexamer is selected from the group consisting of Depakote, Wellbutrin, Allegra, Neurontin, Zovirax, and Claritin. A process for the preparation of a hexameric complex, as described above, from a methylene-bridged tetramer solubilized in an amphiphilic organic solvent. An activator is incorporated into the amphiphilic solvent containing the tetramer. The activator comprises an organic compound of a lower molecular weight than that of the tetramer which is functionalized with at least one of an acidic group, a halogen, an amino group, an amido group, an ester group, or an hydroxy group. The tetramer may be prepared from an aldehyde and pyrogallol which are reacted under conditions to produce a condensation product of the methylene-bridged cyclic tetramer.

18 Claims, 2 Drawing Sheets

Fig. 3

HEXAMERIC COMPLEXES AND THEIR PREPARATION

FIELD OF THE INVENTION

This invention relates to spheroidal hexameric complexes and the preparation of such complexes and their use in providing guest/host assemblies.

BACKGROUND OF THE INVENTION

Various calixarene-type compounds and self-assembled and spherical hexamers have been proposed for various applications. For example, MacGillivray and Atwood in a paper entitled "A Chiral Spherical Molecular Assembly Held Together by 60 Hydrogen Bonds," *Nature*, Vol. 389, pp. 469–472, October 1997, discloses a self-assembly mechanism for methylcalix(4)resorcinarenes self-assembled as a spherical hexamer along with adventitious water molecules. MacGillivray et al disclose the use of methylene-bridged resorcinarenes to form hexameric superstructures. MacGillivray makes reference to exploring various applications including a chiral catalyst for chemical transformations, a micro-vesicle for drug delivery, and an intermediate for separation problems. Subsequent to the MacGillivray/Atwood paper, Gerkensmeier et al in a paper entitled "Self-Assembly of 2,8,14,20-Tetraisobutyl-5,11,17,23-tetrahydroxyresorc(4)arene," *European Journal of Organic Chemistry*, 1999, pp. 2257–2262, discuss self-assembling systems based upon hydroxyresorcinarenes generated by the acid catalyzed condensation of 2-hydroxyresorcinol (pyrogallol) with aldehydes in polar media. Here, the self-assembly products were characterized as two-dimensional polymeric structures held together by hydrogen bonds. The Gerkensmeier et al paper does, however, report on the preparation of a spherical hexamer having an enclosed interior space populated by ten solvent molecules. However, attempts to replicate this hexamer structure were unsuccessful, and the structure was characterized by Gerkensmeier et al as being very fragile due to its being stabilized by weak hydrogen bonds.

SUMMARY OF THE INVENTION

In accordance with the present invention, there is provided a composition of matter comprising a guest/host assembly having a spheroidal host assembly comprised of a methylene-bridged trihydroxybenzene tetramer and a guest component encapsulated within the spheroidal host assembly to provide a highly stable guest/host assembly. The spheroidal host assembly comprises a hexamer characterized by the formula:

(1)

wherein Ar is a trihydroxy benzene radical and CH—R is a substituted methylene bridge between adjacent Ar groups in which R is an aryl or alkylaryl group containing from 6 to 20 carbon atoms, an aliphatic group containing from 2 to 20 carbon atoms, or a substituted aryl or alkylaryl group containing from 6 to 20 carbon atoms, or a substituted aliphatic group containing from 2 to 20 carbon atoms and having a substituent selected from the group consisting of carbonyl, amide, ester, halide, carboxyl, or hydroxy groups.

A guest component, which preferably is a pharmaceutically active agent, is encapsulated within the spheroidal host assembly. The guest/host assembly exhibits a high stability, being stable upon a solubilization in a mixture of acetone and water in a one-to-one ratio for a period of one day at a temperature of 37° C. Preferably, R in Formula (1) is an aliphatic group or a substituted aliphatic group containing from 3 to 13 carbon atoms and more preferably within the range of 3 to 5 carbon atoms. More specifically, R is a $C_3$–$C_5$ alkyl group or a $C_3$–$C_5$ alkyl group substituted with a hydroxy group. Specific R substituents are isobutyl and hydroxy pentyl groups. In yet a further embodiment of the invention, the pharmaceutically active agent encapsulated within the spheroidal hexamer is selected from the group consisting of Depakote, Wellbutrin, Allegra, Neurontin, Zovirax, and Claritin.

In a further aspect of the present invention, there is provided a process for the preparation of a hexameric complex characterized by Formula (1) from a methylene-bridged tetramer solubilized in an amphiphilic organic solvent. The methylene-bridged tetramer is characterized by the formula:

(2)

wherein Ar is a trihydroxy benzene radical and CH—R is a substituted methylene bridge between adjacent Ar groups in which R is an aryl or alkylaryl group containing from 6 to 20 carbon atoms, an aliphatic group containing from 2 to 20 carbon atoms or a substituted aryl, alkylaryl, or aliphatic group having a substituent selected from the group consisting of carbonyl, carboxyl, amide, halide, ester, and hydroxyl groups.

In forming the hexamer of Formula (1) above, an activator is incorporated into the amphiphilic solvent containing the tetramer. The activator comprises an organic compound of a lower molecular weight than that of the tetramer which is functionalized with at least one of an acidic group, a halogen, an amino group, an amido group, an ester group, or an hydroxy group. The solution incorporating the activator and the tetramer is heated at a temperature and for a time sufficient to evaporate the amphiphilic solvent with the attendant crystallization of a spheroidal hexamer characterized by Formula (1). In yet a further aspect of the invention, the tetramer, Formula (2), produced as described above, is contacted with a guest component, preferably a pharmaceutically-active agent, in a second amphiphilic organic solvent, which can be the same as the amphiphilic solvent first referred to above, to provide a dispersion of the hexamer and the guest component in the second solvent. This dispersion of Formula (2) tetramer and guest component is heated at a temperature within the range of 40°–180° C. for at least 12 hours. Thereafter, the second solvent is evaporated to provide the guest component contained within an encapsulating assembly of the spheroidal hexamer. In this aspect of the invention, preferably the dispersion of the tetramer and the guest component is heated at a temperature within the range of 120°–150° C.

In yet a further procedure for preparing a hexameric host/guest complex in accordance with the present invention, there is provided a methylene-bridged tetramer of Formula (2) above solubilized in an amphiphilic organic solvent. A pharmaceutically active agent which has at least one functional carbonyl, amino, or amido group is solubilized in the amphiphilic solvent. The resulting solution is heated at a temperature and for a time sufficient to evaporate the amphiphilic solvent with crystallization of a spheroidal hexamer characterized by Formula (1) above in an encapsulating assembly which contains the pharmaceutical agent in a guest/host complex. Preferably, the pharmaceutically active agent is selected from the group of pharmaceutical agents described above. In carrying out this aspect of the invention, preferably the solution of pharmaceutically active agent and tetramer is heated at a temperature within the range of 20–35° C. for a time within the range of 1–12 hours.

In a further aspect of the invention, there is provided a process for the preparation of a hexameric complex by the reaction of a solution in ethanol of a pyrogallol and an aldehyde characterized by the formula:

(3)

wherein R is an aryl or alkylaryl group having from 6 to 20 carbon atoms or a $C_2$–$C_{20}$ aliphatic group or a substituted aryl, alkylaryl, or aliphatic group having a substituent which is a carbonyl, carboxyl, amide, halide, ester, or hydroxyl group.

The aldehyde and pyrogallol are reacted under conditions to produce a condensation product of a methylene-bridged cyclic tetramer characterized by Formula (2) above. The solution is maintained for a period of time to provide that at least a portion of the tetramer precipitates from solution. Thereafter, the tetramer precipitate is solubilized in a solvent selected from the group consisting of diethyl ether, acetone, or methanol in the presence of an activator selected from the group consisting of nitrobenzene, dichlorobenzene, or other organic compound of lower molecular weight than that of the tetramer which is functionalized with at least one of an acidic group, a halogen, an amino group, an amido group, an ester group, or an hydroxy group. The solution of tetramer and activator is heated at temperature and time conditions sufficient to evaporate the solvent with crystallization of a spheroidal hexamer that is characterized by Formula (1) above.

In yet a further embodiment of the invention, an ethanol solution of pyrogallol and an aldehyde are reacted as described above. The reaction solution is maintained for a period of time to provide that one portion of the tetramer characterized by Formula (2) precipitates from solution while a second portion of the tetramer is retained in solution. The solution containing the second portion of tetramer is mixed with diethyl ether to form an extract of the tetramer and diethyl ether. The extracted solution is then heated at a temperature and for a time sufficient to evaporate the diethyl ether with crystallization of a spheroidal hexamer characterized by Formula (1) as described above. Preferably, an activator is incorporated into the solution which is heated. A preferred activator is an organic compound having a lower molecular weight than the tetramer and functionalized with at least one of an acidic group, a halogen, an amino group, an amido group, an ester group, or an hydroxy group.

DETAILED DESCRIPTION OF THE INVENTION

As indicated by the MacGillivray and the Gerkensmeier papers discussed previously, hexameric superstructures prepared from resorcinol-based calixarenes are known in the art. However, when employing hydroxy resorcinarenes, specifically pyrogallol, the resulting hexamers are considered to be highly fragile since they are stabilized only by weak hydrogen bonds. The present invention proceeds in a manner contrary to the conventional wisdom in producing highly stable hexameric superstructures from methylene-bridged tetramers of trihydroxy benzene. As described in detail below, stable hexameric, spheroidal assembly structures can readily be produced from tetramers of Formula (2) where R is at least $C_3$. Where R is a methyl group attempts to produce spheroidal hexamers from the tetramers are not effective, and where R is an ethyl group, they are effective but with some difficulty.

The present invention is particularly applicable to the formation of host/guest complexes incorporating pharmaceutical agents, and the invention will be described in detail with respect to such agents. However, it is to be recognized that various other applications of the present invention can be employed. Thus, the invention can be employed in such applications as involving catalysts or reactants to chemical reactions or other transformations resulting in desired products. Further materials can be constructed from the hexamers of Formula (1). These materials can be useful in applications of nanotechnology.

Various pharmaceutically-active agents to which the invention may be applied include (1) vaccines to protect against diseases such as tetanus, diphtheria, or whooping cough; (2) growth factors, hormones, and neurotransmitters, e.g. insulin, substance P, adrenaline, LHRH, vasopressin, and oxytocin; and (3) drugs such as anti-cancer agents and antibiotics. Thus, a suitable agent may be administered to humans or other vertebrates to invoke immunity, to supplement hormone levels, to eliminate a disease causing agent, or to provide a therapeutic effect.

Administration of a pharmaceutical agent to the vertebrate involved may be via a number of routes including pulmonary, transdermal, intramuscular, subcutaneous, or oral administration. Intramuscular or subcutaneous administration of the pharmaceutical agent suffers from the disadvantages including the fact that specialized skills are required to administer the pharmaceutical, large scale administration may be difficult to perform; it is expensive; and a number of side reactions can occur to the agent being administered. Thus, oral administration of pharmaceutical agents is often preferred. Many antibiotics (tetracycline, penicillin, etc,)

and hormones (progesterone, estrogen, etc.) can be successfully administered via the oral route. There are, however, drugs, hormones, and immunogens whose efficacy is almost totally lost upon oral administration, including calcitonin, erythropoetin, granulocyte colony stimulating factor, somatostatin, insulin, interferons, and species of DNA and RNA. This loss of efficacy may be due either to the inability of the intestinal mucosa to absorb these compounds or to the breakdown of these substances by various physiological agents in the intestinal milieu.

Specific pharmaceutical agents which can be employed in accordance with the present invention to form a hexamatic host/guest complex include divalproex, sodium hydrogen bis(2-propylpentanoate), available under the trademark Depakote®, *Physicians Desk Reference* (PDR), 53$^{rd}$ Edition, 1999, at pages 428–434; bupropion hydrochloride, (±)-1-(3-chlorophenyl)-2-[(1,1-dimethylethyl)amino]-1-propanone hydrochloride, available under the trademark Wellbutrin® and described in the PDR at pages 1252–1255; loratadine, ethyl 4-(8-chloro-5,6-dihydro-11H-benzo[5,6]cyclohepta[1,2-b]pyridin-11-ylidene)-1-piperidinecarboxylate, available under the designation Claritin® and described in the PDR at pages 2825–2827; acyclovir, 2-amino-1,9-hydro-9-[(2-hydroxyethoxy)methyl]-6H-purin-6-one, available under the designation Zovirax® and described in the PDR at pages 1272–1274; gabapentin, 1-(aminomethyl)cyclohexaneacetic acid, available under the designation Neurontin® and described in the PDR at pages 2301–2304; fexofenadine hydrochloride, (±)-4-[1-hydroxy-4[4-hydroxydiphenylmethyl)-1-piperidinyl]-butyl]-α,α-dimethyl benzeneacetic acid hydrochloride, available under the designation Allegra™ and described in the PDR at pages 1289–1291. For convenience in describing the invention, the aforementioned pharmaceutical agents may be identified herein by reference to their trademarks as indicated previously. For a further description of Depakote®, Wellbutrin®, Claritin®, Zovirax®, Neurontin®, and Allegra™, reference is made to the aforementioned pages designated in the PDR, 53$^{rd}$ Edition, 1999, the entire disclosures of which are incorporated herein by reference.

The tetramer of Formula (2) may be further characterized by the following structural formula:

(4)

wherein R is as described above.

Figure 1:
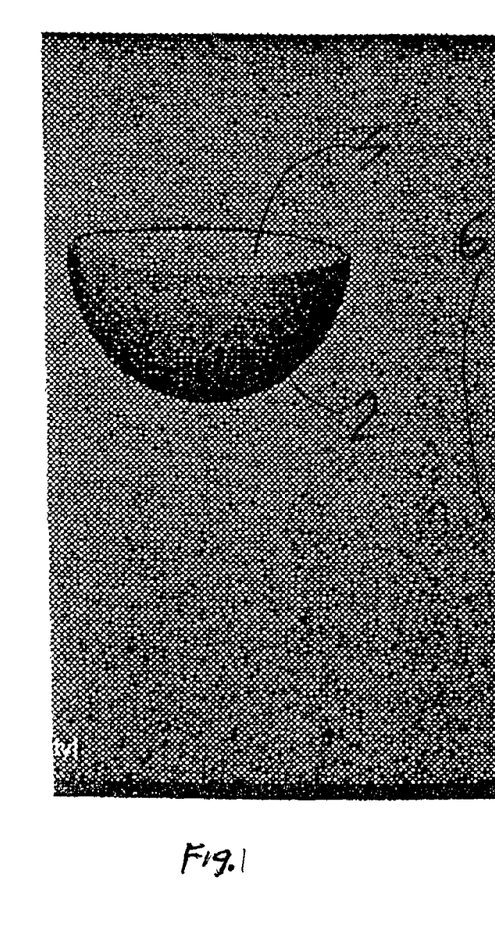
FIG. 1 is an idealized three-dimensional, cup-shaped structure representing a tetramer of the type indicated by Formula (2).
Figure 2:
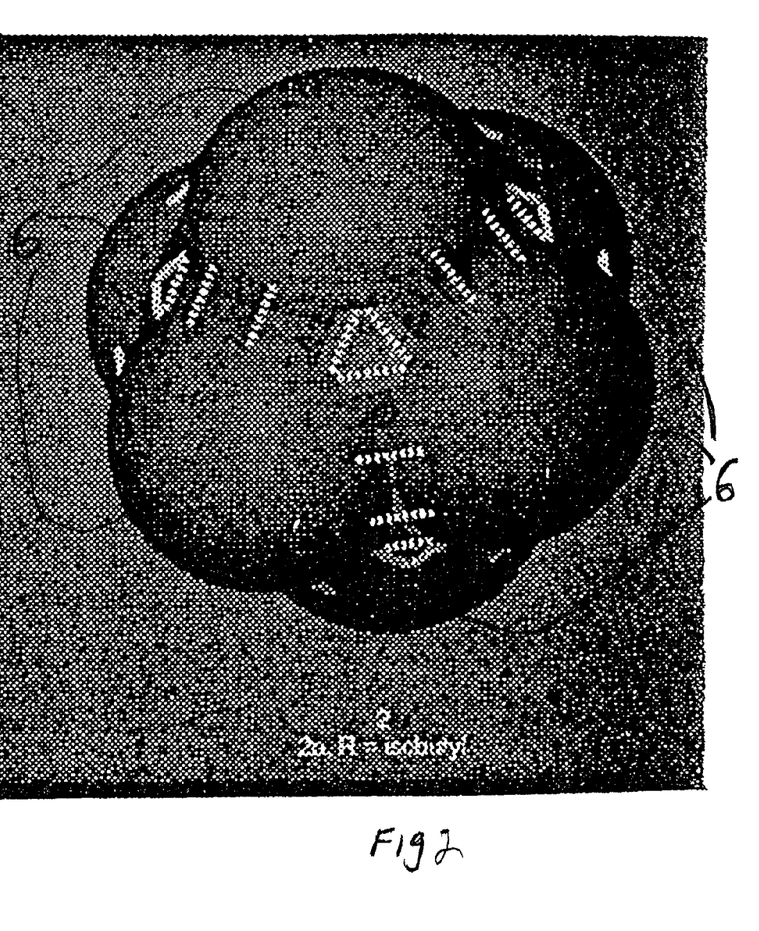
FIG. 2 is a an idealized three-dimensional structure representing a hexamer of the type characterized by the assembly indicated by Formula (1).

Formula (4) may be viewed in its stereochemical configuration as a hemi-spheroidal, cup-shaped structure formed by the four pyrogallol moieties generally defining the wall of the cup and the R substituents projecting outwardly from the cup. The outer surface of the tetramer cup is indicated by reference numeral 2 and the interior space by reference numeral 3. Thus, an idealized schematic, three-dimensional illustration of the tetramer of Formula (4) (without the R groups) is indicated in FIG. 1. When six of the cup-shaped tetramers are assembled to form the spheroidal hexamers involved in the present invention, the resulting structure corresponds to the structure shown schematically in FIG. 2. FIG. 2 is a side elevation of a spheroidal hexamer showing five of the six tetramer structures as indicated by reference numeral 6, with the sixth tetramer structure being hidden from view.

In carrying out a detailed analysis of the hexamer shown in FIG. 2 based upon tetramers derived from pyrogallol, it can be demonstrated that the hexamer is held together by 48 intermolecular hydrogen bonds corresponding to 8 hydrogen bonds per tetramer molecule. This may be contrasted with the corresponding hexamer based upon resorcinol-based tetramers of the type described in MacGillivray, which involves six resorcin(4)arenes and eight water molecules to provide 36 intermolecular hydrogen bonds corresponding to 2.6 hydrogen bonds per water and resorcinol-based tetramer. In accordance with the present invention, the formation of spherical hexamers as based upon pyrogallol tetramers is employed to advantage to provide a highly stable hexameric assembly.

As noted above, the R group formed on the bridge between adjacent trihydroxy benzene groups can be an aliphatic group or an alkylaryl group. Thus, the R group can take the form of a straight or branched-chain alkyl group or a substituted or unsubstituted aryl group. Specifically, R may take the form of a phenyl group or a phenyl group substituted with one or more alkyl substituents. The phenyl group may be directly substituted to the methylene bridge such as may be formed by the reaction of benzaldehyde with pyrogallol. Alternatively, the alkylaryl group may take the form of a phenyl group which may be substituted or unsubstituted, which is connected to the methylene bridge through an alkylene group such as a methylene or ethylene group.

In experimental work carried out respecting the present invention, an acid-catalyzed condensation reaction of pyrogallol and isovaleraldehyde was carried out in 95% ethanol under stirring for 24 hours at a temperature of 23° C. Although higher temperatures, for example, temperatures ranging up to 80°–100° C., can be employed, the present invention is advantageous in that the condensation reaction can be carried out under room temperature conditions. At the conclusion of the reaction, a precipitate containing up to about a 25% yield of the pyrogallol-based tetramer bridged by isobutyl substituted methylene groups was obtained. This product contained no evidence of a corresponding hexamer of the type indicated by Formula (1). While no hexamer was achieved at this point, the tetramer can be converted to the spheroidal hexamer by dissolving the tetramer precipitate in a suitable amphiphilic solvent such as diethyl ether, acetone, or methanol with a few drops of an activating agent such as nitrobenzene or orthodichlorozene followed by crystallization upon slow evaporation. Various other activators may also be employed in recovering the spheroidal hexamer. Such activators include methanol as well as various agents including pharmaceutical agents, such as valproic acid or gabapentin. Where a pharmaceutical agent is employed here, it is encapsulated within the spheroidal hexamer. The hexamer may be recovered by thermal treatment of either the initial precipitate or the initial filtrate as described below.

As an example of a suitable crystallization procedure, 50 mg of pyrogallol(4)arene is dissolved in 15 mL of diethyl ether and 10 drops of nitrobenzene are then added. The diethyl ether is then allowed to evaporate at room temperature. As the diethyl ether evaporates, large crystals of the spheroidal hexamer form slowly over a period of several hours. It would appear that the use of the nitrobenzene or other activator limits the excessive formation of a large number of nucleation sites which could lead to microcrystals.

As noted previously, the spheroidal hexamer can also be recovered by treatment of the tetramer in solution in the filtrate. Here, the solution containing the tetramer is recovered by evaporation of the filtrate to dryness, with the solid then extracted by diethyl ether and the diethyl ether then removed under vacuum. The resulting solid is then dissolved in diethyl ether with a few drops of an activator, such as dichlorobenzene or nitrobenzene. For example, 100 mg of the solid is dissolved in 10 mL of diethyl ether with the addition of 0.3 mL of nitrobenzene. The solution is then allowed to stand with exposure to the atmosphere until crystal formation is observed, usually at a period of four hours or more. The vessel is then closed and allowed to stand with the formation of the hexameric complex formed in about 12 hours. Alternatively, the resulting precipitate is then dissolved in an amphiphilic solvent, such as methanol, ethanol, or propanol. This solution is then heated in a sealed vessel at a temperature within the range of 40–180° C. for a period of at least 12 hours. Preferably, the dispersion of spheroidal hexamer is heated at a temperature within the range of 120°–150° C.

A pharmaceutically active agent as described above may be incorporated into a host/guest assembly of the hexamer by incorporating the drug substance into the methanol or other amphiphilic solvent prior to the heat treatment. Subsequent to the heat treatment, the methanol (or other solvent) is removed under a vacuum of about 10–300 mm Hg at a temperature of about 20–40° C. for a period of about 1–12 hours to yield a solid which may have a red/brown color. Generally, the spheroidal hexamer is colorless except for color associated with guest components, and if a red/brown color of the precipitator is found, this is probably due to quinone byproducts in relatively low concentrations. These byproducts may be removed by a purification step involving a crystallization procedure involving extraction with diethyl ether, as described previously, to produce in this case the spheroidal hexamer with the presence of a guest component which is essentially colorless.

Figure 3:
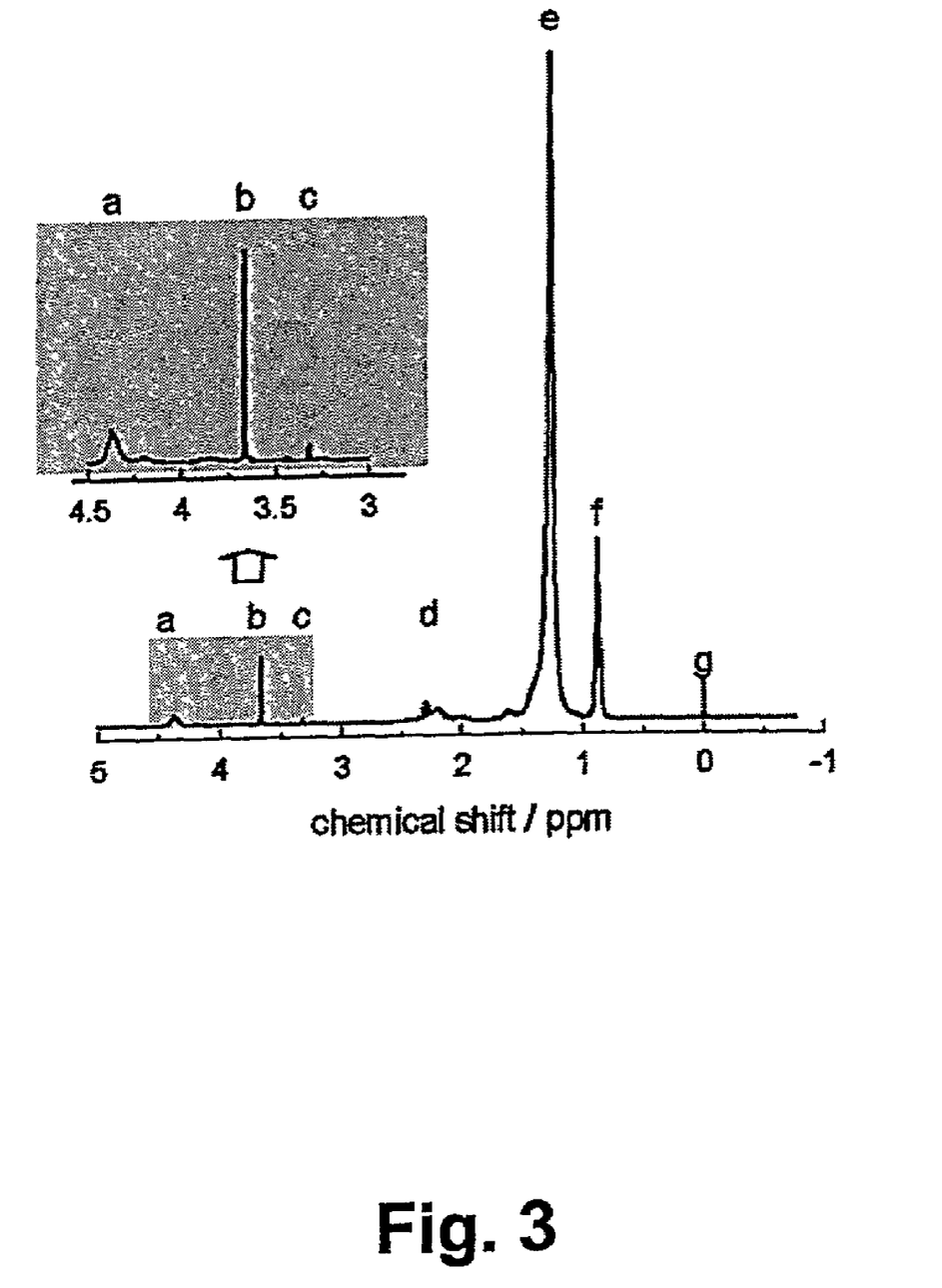
FIG. 3 is a NMR spectrum of a hexamer of the type indicated by Formula (1).

Nuclear magnetic resonance (NMR) spectroscopic investigations were carried out to verify the existence of the spheroidal hexamer in solution. A representative experiment produced the $^1$H NMR spectrum of the hexamer, thermally treated with methanol as described above, in deuterochloroform as illustrated in FIG. 3, in which chemical shift/ppm is plotted on the abscissa versus relative peak amplitude on the ordinate. FIG. 3 is the $^1$H NMR spectrum of C-tridecylpyrogallol(4)arene at room temperature in deuterochloroform with TMS (tetramethylsilane). The enlarged inset in FIG. 3 is the region of the spectrum displaying the methanol resonances. The peak assignments a, b, and c in the enlarged inset are for diaryl C—H, $CH_3$ of the methanol guest, and $CH_3$ of the methanol in the bulk solvent, respectively. Peak assignments d, e, and f are for the $CH_2$ moiety adjacent to CH in the bridging group, the remaining $CH_2$ groups, and the terminal $CH_3$ group, respectively, on the R substituent. Peak g is the TMS internal standard.

The most significant features in the spectrum of FIG. 3 are the two methanol peaks, b and c, indicating, respectively, the methanol trapped within the hexameric spheroidal assembly and the methanol in the bulk solvent. Similar work was carried out in $d^6$-acetone, $d^6$-dimethyl sulfoxide, and $d^8$-toluene. NMR spectra for the spheroidal hexamer synthesized in ethanol or isopropanol also showed two sets of resonances for each equivalent portion of the ethanol or isopropanol molecules in the spheroidal guest/host assembly and the solvent. A corresponding NMR sample tube, sealed under a pressure of 1 atm (at 25° C.) and then heated to a temperature of 150° C. with the pressure in the sealed tube of about 1.4 atmospheres, showed no changes in the intensities of peaks b and c for methanol and for acetone. Thus, it was established that methanol molecules within a hexameric sphere do not exchange with methanol in the bulk solvent or with the bulk solvent itself and that the guest/host assembly in which methanol is a guest within the spheroidal hexamer is stable at 150° C. in $d^6$-acetone.

The hexameric capsules can be characterized in terms of their crystallographic structures. The hexameric capsules for R=isobutyl have been found to crystallize as crystals having rhombohedral or triclinic symmetry. In the rhombohedral space group, two axes are equal and unequal with the third axis, and in the triclinic space groups, all three axes are unequal. In the rhombohedral space group $R_3$ bar the unit cell has a and b each equal to 38.84 Å with c equal to 24.04 Å. For the triclinic space group P1 bar, it has been found that a=21.713, b=21.722, c=21.944 Å, alpha=63.86°, beta=85.33°, and gamma =60.93°. The crystals of the hexameric capsules can therefore be characterized by a unit cell in which a, b, and c are at least 20 Å or more.

Using the evaluation techniques described above, stable hexameric spheroidal assemblies corresponding to Formula (1), in which R is n-propyl, n-butyl, isobutyl, n-pentyl—tridecyl, have been readily produced. Where the R substituent is an ethyl group, a spheroidal hexameric assembly corresponding to Formula (1) can be produced, although it is somewhat less stable than the corresponding compound in which R is a propyl group. Stable spheroidal hexamers characterized by Formula (1), in which R ranges up to a $C_{20}$ aliphatic group, can be produced in which a stable host/guest spheroidal assembly can be obtained.

The solubility of the spheroidal hexamer is relatively low in apolar solvents when the aliphatic group R is of a relatively short chain length, e.g. 3 or 4 carbon atoms. Similar low solubility occurs in polar solvents when the aliphatic chain length of R is relatively long, e.g. 10–13 carbon atoms, or possibly longer ranging up to 20 carbon atoms. It is thus possible, with the appropriate choice of the R group, to provide for stable spheroidal hexamers in polar or apolar solvents. For R=—$CH_2CH_2CH_2CH_2OH$, stable, water-soluble hexameric capsules are produced. For the purpose of delivery of a pharmaceutical agent to a suitable biologic site as described above, water will be the preferred solvent.

As indicated previously, it is possible, in accordance with the present invention, to provide spheroidal hexameric host/guest assemblies which are highly soluble in water. The spheroidal hexamers are also highly stable in mixtures of acetone and water. Thus, the spheroidal hexamer characterized by Formula (1). in which R is an n-pentyl group, is highly stable in a mixture of acetone and water. Specifically, a host/guest assembly of this hexamer, in which R is a pentyl group with methanol as a guest component, is stable upon solubilization of acetone and water in a 1:1 ratio for prolonged periods of time. Such guest/host assemblies easily meet the standard established above of a guest/host assembly which is stable upon solubilization of water and acetone in a 1:1 mixture for a period of at least one day at a temperature of 37° C. This stability applies both to the structural integrity of the spheroidal hexamer imparted by the above-described hydrogen bonding arrangement as well as to the fact that the entrapped methanol encapsulated by the spheroidal hexamer will not exchange into the bulk solvent. The term "stability," as used herein, means that such exchange does not occur beyond a minor amount, specifically no more than about 5% of the guest component exchanged into the surrounding medium over a period of one day at a temperature of 37° C.

As indicated previously, the spheroidal hexameric assembly completely encloses the interior space defined by the hexamer so that the resulting "capsule" completely encloses the space within the capsule. The interior volume of the capsule is about 1510 Å$^3$. The interior volume exhibits an enclosed space which is approximately spherical in shape with an additional octahedral arrangement of six small bulges, i.e., the clefts of the individual cup-shaped tetramer building blocks which contribute to the total volume of the cavity. Hydrogen bond donor or acceptor groups do not project into this enclosed space, and thus there is no mechanism provided for ordering the contents.

The spheroidal hexameric assembly exists in solution similarly as it exists in the solid state. NMR analysis indicates, by reference to FIG. 3, that a capsule-like structure exists in solution, and integration of the methyl proton signal and diaryl C—H signals b and a, respectively, of FIG. 3, are consistent with an enclosure of about 18 methanol molecules in the case where a methanol guest assembly is involved. The free volume of 1510 Å$^3$, as calculated from the solid state structure, provides space for about 23 methanol molecules, thus indicating that the assembly in solution contains a comparable amount of interior space as the solid state hexameric assembly and demonstrating that the solid state structure is maintained in solution.

The following examples illustrate various hexameric spheroidal capsules and complexes of such capsules in a host/guest relationship and methods of their preparation.

EXAMPLE 1

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 2.85 mL propionaldehyde, dropwise with stirring. The solution was allowed to stir for 12 hours, at which time a white precipitate was observed. The solution was filtered affording 0.95 g of white solid and a lightly colored filtrate. Mass spectroscopic analysis showed that the tetramer, characterized by Formula (2) in which R is ethyl, had formed in high yield in both the solid and the filtrate. The hexameric capsules were obtained as detailed in Examples 2–10 below.

EXAMPLE 2

100 mg of the white solid of Example 1 was dissolved in 10 mL diethyl ether, and 0.3 mL nitrobenzene was added. This solution was allowed to stand open in a hood until crystal formation was observed (ca. 4 hours). The vessel was then loosely capped, whereupon a mass of crystals of the hexameric capsule, corresponding to Formula (1) in which R is ethyl, formed (in ca. 12 hours).

EXAMPLE 3

100 mg of the white solid of Example 1 was dissolved in 10 mL methanol, and 0.3 mL nitrobenzene was added. This solution was allowed to stand open in a hood until crystal formation was observed (ca. 12 hours). The vessel was then loosely capped, whereupon a mass of crystals of the hexameric capsule formed (in ca. 12 hours).

EXAMPLE 4

100 mg of the white solid produced in Example 1 was dissolved in 10 mL acetone, and 0.3 mL nitrobenzene was added. This solution was allowed to stand open in a hood until crystal formation was observed (ca. 6 hours). The vessel was then loosely capped, whereupon a mass of crystals of the hexameric capsule formed (in ca. 12 hours).

EXAMPLE 5

100 mg of the white solid produced in Example 1 was dissolved in 10 mL diethyl ether, and 0.3 mL o-dichlorobenzene was added. This solution was allowed to stand open in a hood until crystal formation was observed (ca. 12 hours). The vessel was then loosely capped, whereupon a mass of crystals of the hexameric capsule formed (in ca. 12 hours).

EXAMPLE 6

100 mg of the white solid produced in Example 1 was dissolved in 10 mL diethyl ether, and 0.3 g gabapentin was added. This solution was allowed to stand open in a hood until crystal formation was observed (ca. 12 hours). The vessel was then loosely capped, whereupon a mass of crystals of the hexameric capsule formed (in ca. 12 hours).

EXAMPLE 7

100 mg of the white solid produced in Example 1 was dissolved in 10 mL diethyl ether, and 0.3 mL nitrobenzene was added. This solution was placed in a vacuum desiccator until crystal formation was observed (ca. 15 minutes). The vessel was then removed from the desiccator and loosely capped, whereupon a mass of crystals of the hexameric capsule formed (in ca. 12 hours).

EXAMPLE 8

The filtrate recovered from the filtration in Example 1 was evaporated under a slight vacuum at about 50° C. to dryness on a rotary evaporator. The solid was then extracted with diethyl ether, and the diethyl ether was removed under vacuum. 100 mg of the resulting solid was dissolved in 10 mL diethyl ether, and 0.3 mL nitrobenzene was added. This solution was allowed to stand open in a hood until crystal formation was observed (ca. 4 hours). The vessel was then loosely capped, whereupon a mass of crystals of the hexameric capsule formed (in ca. 12 hours).

EXAMPLE 9

The filtrate from Example 1 was evaporated to dryness on a rotary evaporator. The solid was then extracted with diethyl ether, and the diethyl ether was removed under vacuum. The solid was then dissolved in methanol. The methanol solution was heated in a sealed tube to 120–150° C. for 12 hours. Methanol was then removed under vacuum to yield a solid. 100 mg of this solid was dissolved in 10 mL diethyl ether, and 0.3 mL nitrobenzene was added. This solution was allowed to stand open in a hood until crystal formation was observed (ca. 4 hours). The vessel was then loosely capped, whereupon a mass of crystals of the hexameric capsule formed (in ca. 12 hours).

EXAMPLE 10

The solid precipitate from Example 1 was dissolved in methanol. The methanol solution was heated in a sealed tube to 120–150° C. for 12 hours. Methanol was then removed under vacuum to yield a solid. 100 mg of this solid was dissolved in 10 mL diethyl ether, and 0.3 mL nitrobenzene was added. This solution was allowed to stand open in a hood until crystal formation was observed (ca. 4 hours). The vessel was then loosely capped, whereupon a mass of crystals of the hexameric capsule formed (in ca. 12 hours).

EXAMPLE 11

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 3.60 mL butyraldehyde, dropwise with stirring. The solution was allowed to stir for 12 hours, at which time a white precipitate was observed. The solution was filtered affording 0.80 g of white solid and a lightly colored filtrate. Mass spectroscopic analysis showed that the tetramer, characterized by Formula (2) in which R is a n-propyl group, had formed in high yield in both the solid and the filtrate. The corresponding hexameric capsules were obtained following procedures described above with reference to Examples 2–10.

EXAMPLE 12

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 4.25 mL isovaleraldehyde, dropwise with stirring. The solution was allowed to stir for 12 hours, at which time a white precipitate was observed. The solution was filtered affording 1.05 g of white solid and a lightly colored filtrate. Mass spectroscopic analysis showed that the tetramer, characterized by Formula (2) in which R is isobutyl, had formed in high yield in both the solid and the filtrate. The corresponding hexameric capsules were obtained following procedures described above with reference to Examples 2–10.

EXAMPLE 13

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 4.25 mL n-valeraldehyde, dropwise with stirring. The solution was allowed to stir for 12 hours, at which time a white precipitate was observed. The solution was filtered affording 0.85 g of white solid and a lightly colored filtrate. Mass spectroscopic analysis showed that the tetramer, characterized by Formula (2) in which R is n-butyl, had formed in high yield in both the solid and the filtrate. The corresponding hexameric capsules were obtained following procedures described above with reference to Examples 2–10.

EXAMPLE 14

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 4.80 mL of hexanol, dropwise with stirring. The solution was allowed to stir for 12 hours, at which time a white precipitate was observed. The solution was filtered affording 0.55 g of white solid and a lightly colored filtrate. Mass spectroscopic analysis showed that the tetramer, characterized by Formula (2) in which R is n-pentyl, had formed in high yield in both the solid and the filtrate. The corresponding hexameric capsules were obtained following procedures described above with reference to Examples 2–10.

EXAMPLE 15

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 4.80 mL 5-hydroxypentanal, dropwise with stirring. The solution was allowed to stir for 12 hours, at which time a white precipitate was observed. The solution was filtered affording 0.90 g of white solid and a lightly colored filtrate. Mass spectroscopic analysis showed that the tetramer, indicated by Formula (2) in which R is a 4-hydroxy butyl group, had formed in high yield in both the solid and the filtrate. The corresponding hexameric capsules were obtained following procedures described above with reference to Examples 2–10.

EXAMPLE 16

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 6.90 mL nonyl aldehyde, dropwise with stirring. The solution was allowed to stir for 12 hours, at which time a white precipitate was observed. The solution was filtered affording 0.90 g of white solid and a lightly colored filtrate. Mass spectroscopic analysis showed that the tetramer, characterized by Formula (2) in which R is an octyl group, had formed in high yield in both the solid and the filtrate. The corresponding hexameric capsules were obtained following procedures described above with reference to Examples 2–10.

EXAMPLE 17

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 8.30 mL undecyl aldehyde, dropwise with stirring. The solution was allowed to stir for 3 hours, at which time a precipitate was observed. The solution was filtered affording 2.00 g of solid and a lightly colored filtrate. Mass spectroscopic analysis showed that the tetramer with R=n-decyl had formed in high yield in both the solid and the filtrate. The hexameric capsules were obtained as follows.

The solid precipitate from the initial reaction was dissolved in methanol. The methanol solution was heated in a sealed tube to 120–150° C. for 12 hours. Methanol was then removed under vacuum to yield the hexameric capsules as a solid.

EXAMPLE 18

The procedure in Example 17 was followed, except that the solid precipitate from the initial reaction was dissolved in methanol. The methanol solution was heated in a sealed tube to 120–150° C. for 12 hours. Methanol was then removed under vacuum to yield a solid. 100 mg of this solid was dissolved in 10 mL diethyl ether, and 0.3 mL nitrobenzene was added. This solution was allowed to stand open in a hood until crystal formation was observed (ca. 4 hours). The vessel was then loosely capped, whereupon a mass of solid of the hexameric capsules formed (in ca. 12 hours).

EXAMPLE 19

The method procedure in Example 17 was followed, except that the filtrate from the filtration of the initial reaction was evaporated to dryness on a rotary evaporator at 50° C. under a vacuum supplied by an aspirator. The solid was then dissolved in methanol. The methanol solution was heated in a sealed tube to 120–150° C. for 12 hours. Methanol was then removed under vacuum to yield the hexameric capsules as a solid.

EXAMPLE 20

The procedure in Example 17 was followed, except that the filtrate from the filtration of the initial reaction was evaporated to dryness on a rotary evaporator. The solid was then extracted diethyl ether, and the diethyl ether was removed under vacuum. The solid was then dissolved in methanol. The methanol solution was heated in a sealed tube to 120–150° C. for 12 hours. Methanol was then removed under vacuum to yield a solid. 100 mg of this solid can be dissolved in 10 mL diethyl ether, and 0.3 mL nitrobenzene can be added. This solution can be allowed to stand open in a hood until crystal formation is observed (ca. 4 hours). The vessel can then be loosely capped, whereupon a mass of crystals of the hexameric capsules will form (in ca. 12 hours).

EXAMPLE 21

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 8.48 g tetradecyl aldehyde with stirring. The solution was allowed to stir for 6 hours, at which time a precipitate was observed. The solution was filtered affording 2.40 g of solid and a colored filtrate. Mass spectroscopic analysis showed that the tetramer with R=n-tridecyl had formed in high yield in both the solid and the filtrate. The hexameric capsules were obtained as follows.

The filtrate from the filtration of the initial reaction was evaporated to dryness on a rotary evaporator at 50° C. under a vacuum supplied by an aspirator. The solid was then dissolved in methanol. The methanol solution was heated in a sealed tube to 120–150° C. for 12 hours. Methanol was then removed under vacuum to yield the hexameric capsules as a solid.

EXAMPLE 22

The procedure of Example 21 was followed, except that the initial precipitate was dissolved in methanol. The methanol solution was heated in a sealed tube to 120–150° C. for 12 hours. Methanol was then removed under vacuum to yield the hexameric capsules as a solid.

EXAMPLE 23

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 4.05 mL benzaldehyde, dropwise with stirring. The solution was allowed to stir for 12 hours, at which time a precipitate was observed. The solution was filtered affording 1.05 g of solid and a lightly colored filtrate. Mass spectroscopic analysis showed that the tetramer with R=phenyl had formed in high yield in both the solid and the filtrate. The hexameric capsules can be obtained as follows.

The solid precipitate from the initial reaction can be dissolved in methanol. The methanol solution can be heated in a sealed tube to 120–150° C. for 12 hours. Methanol can then be removed under vacuum to yield the hexameric capsules as a solid.

EXAMPLE 24

To 25 mL 95% ethanol was added 5.00 g pyrogallol (1,2,3-trihydroxybenzene). The pyrogallol dissolved readily with stirring. Six mL of concentrated HCl was added dropwise with stirring. To this solution was added 4.25 mL isovaleraldehyde, dropwise with stirring. The solution was allowed to stir for 12 hours, at which time a white precipitate was observed. The solution was filtered affording 1.05 g of white solid and a lightly colored filtrate. Mass spectroscopic analysis showed that the tetramer had formed in high yield in both the solid and the filtrate. The hexameric capsules with gabapentin as the guest/host component were obtained by the following method.

The initial precipitate was mixed in a 1:1 ratio with gabapentin and dissolved in methanol. The methanol solution was heated in a sealed tube to 120–150° C. for 12 hours. Methanol was then removed under vacuum to yield the hexameric capsules as a solid with gabapentin included within the capsules.

EXAMPLE 25

The procedure of Example 24 was followed, except that the filtrate from the filtration of the initial reaction was evaporated to dryness on a rotary evaporator at 50° C. under a vacuum supplied by an aspirator. The solid was then dissolved in methanol along with a 1:1 ratio of gabapentin. The methanol solution was heated in a sealed tube to 120–150° C. for 12 hours. Methanol was then removed under vacuum to yield the hexameric capsules as a solid with gabapentin included within the capsules in a host/guest relationship.

EXAMPLE 26

The procedure of Example 24 was followed, except that the initial precipitate was mixed in a 1:1 ratio with valproic acid and dissolved in methanol. The methanol solution was heated in a sealed tube to 120–150° C. for 12 hours. Methanol was then removed under vacuum to yield the hexameric capsules as a solid with valproic acid included within the capsules.

EXAMPLES 27

The procedure of Example 25 was followed, except that valproic acid was used in place of gabapentin.

EXAMPLE 28

The procedure of Example 26 was followed, except that isopropyl alcohol was used in place of methanol.

EXAMPLE 29

The procedure of Example 24 was followed, except that fexofenadine hydrochloride was used in place of gabapentin.

EXAMPLE 30

The procedure of Example 24 was followed, except that fexofenadine was used in place of gabapentin.

EXAMPLE 31

The procedure of Example 25 can be followed, except that fexofenadine or fexofenadine hydrochloride was used in place of gabapentin.

EXAMPLE 32

The procedure of Example 24 can be followed, except that bupropion can be used in place of gabapentin.

EXAMPLE 33

The procedure of Example 25 can be followed, except that bupropion can be used in place of gabapentin.

EXAMPLE 34

The procedure of Example 29 can be followed, except that loratadine or loratadine hydrochloride can be used in place of fexofenadine.

EXAMPLE 35

The procedure of Example 26 can be followed, except that loratadine or loratadine hydrochloride can be used in place of fexofenadine or fexofenadine hydrochloride.

EXAMPLE 36

The procedure of Example 24 can be followed, except that acyclovir can be used in place of gabapentin.

EXAMPLE 37

The procedure of Example 25 can be followed, except that acyclovir can be used in place of gabapentin.

Having described specific embodiments of the present invention, it will be understood that modifications thereof may be suggested to those skilled in the art, and it is intended to cover all such modifications as fall within the scope of the appended claims.

What is claimed:

1. A process for the preparation of an hexameric complex comprising:
   (a) providing a methylene-bridged tetramer of trihydroxybenzene characterized by the formula:

wherein Ar is a trihydroxybenzene radical and CH—R is a substituted methylene bridge between adjacent Ar groups in which R is an aryl or alkylaryl group containing from 6 to 20 carbon atoms, an aliphatic group containing from 2 to 20 carbon atoms, or a substituted aliphatic or aryl or alkylaryl group having a substituent selected from the group consisting of carbonyl, carboxyl, amide, halide, ester, and hydroxyl groups, solubilized in an amphiphilic organic solvent;
   (b) incorporating into said amphiphilic solvent an activator comprising an organic compound of a lower molecular weight than said tetramer and functionalized with at least one of an acidic group, a halogen, an amino group, an amido group, an ester group, and a hydroxy group; and
   (c) heating said solution at a temperature and a time sufficient to evaporate at least a portion said amphiphilic solvent with crystallization of a spheroidal hexamer characterized by the formula:

wherein Ar and R are as defined above.

2. The method of claim 1 wherein R is an aliphatic group or a substituted aliphatic group containing from 3 to 13 carbon atoms.

3. A process for the preparation of an hexameric complex comprising:
   (a) providing a methylene-bridged tetramer of trihydroxybenzene characterized by the formula:

wherein Ar is a trihydroxybenzene radical and CH—R is a substituted methylene bridge between adjacent Ar groups in which R is an aryl or alkylaryl group containing from 6 to 20 carbon atoms, an aliphatic group containing from 2 to 20 carbon atoms, or a substituted aliphatic or aryl or alkylaryl group having a substituent selected from the group consisting of carbonyl, carboxyl, amide, halide, ester, and hydroxyl groups, solubilized in an amphiphilic organic solvent;
   (b) incorporating into said amphiphilic solvent an activator comprising an organic compound of a lower molecular weight than said tetramer and functionalized with at least one of an acidic group, a halogen, an amino group, an amido group, an ester group, and a hydroxy group;
   (c) heating said solution at a temperature and a time sufficient to evaporate at least a portion said amphiphilic solvent with crystallization of a spheroidal hexamer characterized by the formula:

wherein Ar and R are as defined above; and
  (d) further comprising contacting said tetramer with a guest component in a second amphiphilic organic solvent to provide a dispersion of said tetramer and said guest component in said second solvent, heating said dispersion of tetramer and guest component in said second solvent at a temperature within the range of 40–180° C. for a period of at least 12 hours, and thereafter evaporating said second solvent to provide said guest substance contained within an encapsulating assembly of spheroidal hexamer.

4. The method of claim 3 wherein said dispersion of said tetramer and said guest component is heated at a temperature within the range of 120–150° C.

5. The method of claim 3 wherein said second amphiphilic organic solvent is selected from the group consisting of methanol, ethanol, or propanol.

6. The method of claim 3 wherein said guest component is a pharmaceutically active agent.

7. The method of claim 6 wherein R is a $C_3$–$C_5$ alkyl group or a $C_3$–$C_5$ alkyl group substituted with a hydroxy group.

8. The method of claim 7 wherein R is an n-propyl, n-butyl, i-butyl, or n-pentyl group.

9. The method of claim 7 wherein R is an isobutyl group.

10. The method of claim 7 wherein R is —$CH_2CH_2CH_2CH_2OH$.

11. A process for the preparation of an hexameric complex comprising:
  (a) providing a methylene-bridged tetramer of trihydroxybenzene characterized by the formula:

wherein Ar is a trihydroxybenzene radical and CH—R is a substituted methylene bridge between adjacent Ar groups in which R is an aryl or alkylaryl group containing from 6 to 20 carbon atoms, an aliphatic group containing from 2 to 20 carbon atoms, or a substituted aliphatic or aryl or alkylaryl group having a substituent selected from the group consisting of carbonyl, carboxyl, amide, halide, ester, and hydroxyl groups, solubilized in an amphiphilic organic solvent;
  (b) incorporating into said amphiphilic solvent an activator comprising an organic compound of a lower molecular weight than said tetramer and functionalized with at least one of an acidic group, a halogen, an amino group, an amido group, an ester group, and a hydroxy group; and
  (c) heating said solution at a temperature and a time sufficient to evaporate at least a portion said amphiphilic solvent with crystallization of a spheroidal hexamer characterized by the formula:

wherein Ar and R are as defined above; and
  (d) wherein said activator comprises a pharmaceutically active agent having at least one carboxyl, halide, ester, hydroxyl, carbonyl, amino or amide group wherein said spherical hexamer is crystallized in an encapsulating assembly which contains said pharmaceutical agent in a guest/host complex.

12. The process of claim 11 wherein said pharmaceutically active agent is selected from the group consisting of divalproex sodium, bupropion hydrochloride, fexofenadine hydrochloride, gabapentin, loratadine and acyclovir.

13. The process of claim 11 wherein R contains from 3 to 5 carbon atoms.

14. The process of claim 13 wherein R is a $C_3$–$C_5$ alkyl group or a $C_3$–$C_5$ alkyl group substituted with a hydroxyl group.

15. A process for the preparation of a hexameric complex comprising:
  (a) producing a methylene bridged tetramer of trihydroxybenzene as set forth in paragraph (c) by reacting a solution in ethanol of pyrogallol and an aldehyde characterized by the formula:

wherein R is an aryl or alkylaryl group containing from 6 to 20 carbon atoms, an aliphatic group containing from 2 to 20 carbon atoms, or a substituted aliphatic or aryl or alkylaryl group having a substituent selected from the group consisting of carbonyl, carboxyl, amide, halide, ester, and hydroxyl groups, under conditions to produce a condensation product of said methylene-bridged cyclic tetramer;
  (b) maintaining said solution for a period of time to provide that at least a portion of said tetramer precipitates from said solution;
  (c) thereafter providing a methylene-bridged tetramer of trihydroxybenzene characterized by the formula:

wherein Ar is a trihydroxybenzene radical and CH—R is a substituted methylene bridge between adjacent Ar groups in which R is an aryl or alkylaryl group containing from 6 to 20 carbon atoms, an aliphatic group containing from 2 to 20 carbon atoms, or a substituted aliphatic or aryl or alkylaryl group having a substituent selected from the group consisting of carbonyl, carboxyl, amide, halide, ester, and hydroxyl groups, solubilized in an amphiphilic organic solvent;

(d) incorporating into said amphiphilic solvent an activator comprising an organic compound of a lower molecular weight than said tetramer and functionalized with at least one of an acidic group, a halogen, an amino group, an amido group, an ester group, and a hydroxy group; and (e) heating said solution at a temperature and a time sufficient to evaporate at least a portion said amphiphilic solvent with crystallization of a spheroidal hexamer characterized by the formula:

wherein Ar and R are as defined above.

16. The process claim 15 wherein said activator is selected from the group consisting of methanol, nitrobenzene and dichlorobenzene.

17. The process of claim 15 wherein said activator is a pharmaceutically active agent having a lower molecular weight than said tetramer.

18. The process of claim 15 wherein R is a $C_3$–$C_5$ alkyl group or a $C_3$–$C_5$ alkyl group substituted with a hydroxyl group.

* * * * *